(12) United States Patent
Leon Fong et al.

(10) Patent No.: US 6,339,913 B1
(45) Date of Patent: *Jan. 22, 2002

(54) METHOD FOR IMPROVING THE OSTEOINTEGRATION OF OSSEUS FIXING IMPLANTS

(75) Inventors: Betty Mireya Leon Fong; Juan Maria Pou Saracho; Jorge Luis Arias Otero; Francisco Jose Garcia Sanz; Mercedes Belen Mayor Leiros; Pio Manuel Gonzalez Fernandez; Mariano Jesus Perez-Martinez Y Perez-Amor, all of Vigo (ES)

(73) Assignee: Universidad de Vigo (ES)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/113,584

(22) Filed: Jul. 10, 1998

Related U.S. Application Data

(63) Continuation of application No. PCT/ES97/00269, filed on Nov. 10, 1997.

(30) Foreign Application Priority Data

Nov. 12, 1996 (ES) ................................ 9602439

(51) Int. Cl.⁷ .................. B65B 55/04; B65B 55/12; C23C 14/28; A61F 2/30; A61L 27/02; A61L 27/28
(52) U.S. Cl. .................. 53/425; 53/432; 427/2.27; 623/16.11
(58) Field of Search .............. 53/425, 428, 432, 53/411; 427/2.27; 623/16.11

(56) References Cited

U.S. PATENT DOCUMENTS

| | | | | |
|---|---|---|---|---|
| 4,065,816 A | * | 1/1978 | Sawyer | 53/425 |
| 4,712,681 A | * | 12/1987 | Branemark et al. | 53/425 X |
| 4,908,030 A | | 3/1990 | Linkow | |
| 4,944,754 A | | 7/1990 | Linkow | |
| 5,141,576 A | * | 8/1992 | Shimamune et al. | 427/2.27 |
| 5,242,706 A | | 9/1993 | Cotell | |
| 5,279,831 A | | 1/1994 | Constantz | |
| 5,314,475 A | | 5/1994 | Repenning | |
| 5,543,019 A | | 8/1996 | Lee | |
| 5,603,338 A | * | 2/1997 | Beaty | 427/2.27 |
| 5,674,292 A | | 10/1997 | Tucker | |

FOREIGN PATENT DOCUMENTS

| | | |
|---|---|---|
| WO | 94/25637 | 10/1994 |
| WO | 96/16196 | 5/1996 |
| WO | 96/40297 | 12/1996 |

* cited by examiner

*Primary Examiner*—Stephen F. Gerrity
(74) *Attorney, Agent, or Firm*—Baker Botts LLP

(57) ABSTRACT

The osteointegration of osseous fixing implants may be improved through a series of surface treatments. These treatments comprise a cleaning and passivation process, the application of a coating of $Ca_UP_VH_xO_yC_z$ to the implant, where subindexes u, v, x, y, and z are natural numbers including zero with variable stoichiometry, and a sterilization process by irradiation. The flexibility of this method provides for the control of physical and chemical properties of the obtained surface in order to match the properties with those of the bone in which the implant will be placed.

10 Claims, 1 Drawing Sheet

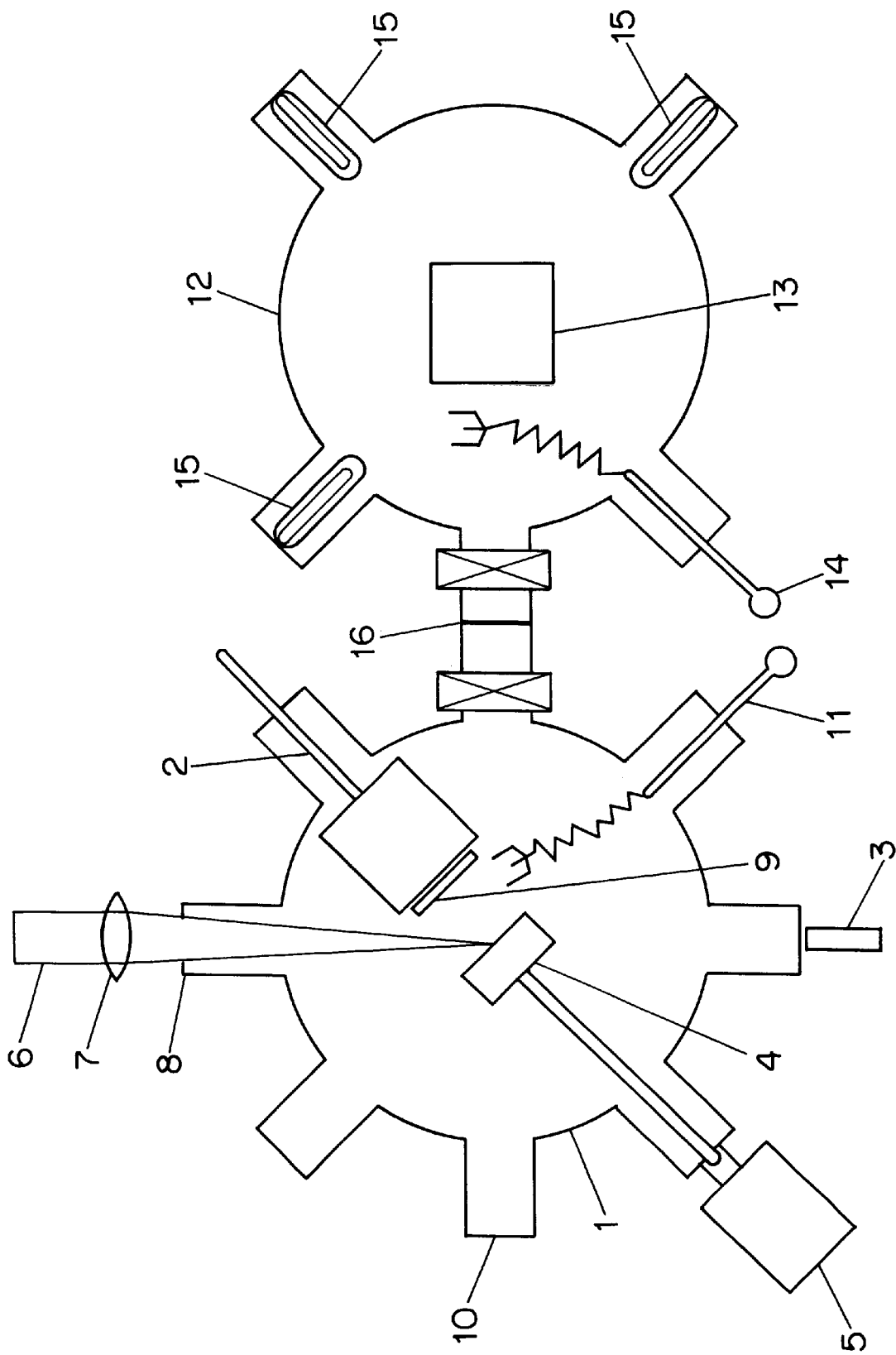

METHOD FOR IMPROVING THE OSTEOINTEGRATION OF OSSEUS FIXING IMPLANTS

The present application is a continuation of PCT/ES97/00269 filed Nov. 10, 1997. The present invention refers to a method for improving the osteointegration of implants for orthopedic and odontology applications.

This invention provides a series of treatments on osseous fixing implant surfaces, such that the implant subject to the treatment improves substantially its osteointegration properties with respect to the bone with which the implant will be in contact. These treatments comprise a cleaning and passivation process, the application of a Ca—P—H—O—C system coating (i.e., a compound of formula $Ca_U P_V H_X O_Y C_Z$ where subscripts u, v, x, y, and z are natural numbers including zero) by means of a laser ablation technique, and sterilization by an irradiation process.

When the replacement of a defective member of a human body is required, the best solution would be the use of compatible tissue or organ provided by a human donor, since natural tissues and organs contain the right proportions of materials needed to satisfy the body functions. However, because of increasing demand for transplants, there are not enough human donors to satisfy the need for living implants. On the other hand, when natural implants are used, frequently rejection problems appear in the receiving body.

A solution to meet the increasing demand for transplants is the use of manmade tissues and organs. Since 1950 continuous research has been performed on biomaterials and non-pharmacological products that are adequate to improve or substitute for the functions of human organs and tissues.

Present biomaterials are useful for many applications, ranging from substitution of intraocular lenses to the manufacture of artificial hearts. Generally, a biomaterial can be defined as a mechanically and biologically compatible material, i.e., it must stand the mechanical stresses derived from its function, and be non-toxic, controllable, and predictable in its interaction with the human body.

In particular, a set of specifications can be defined, which the biomaterials should meet (see, for example: S. F. Hulbert "Use of Ceramics in Surgical Implants", ed. By S. F. Hulbert and F. A. Young, Gordon and Breach Science Publishers, New York (1969)).

The biomaterials should have the following characteristics: a) resistance to the action of body fluids; b) an ability to withstand the mechanical stresses inherent in the required functions; c) an ability to adapt to the required shape; d) an absence of resulting toxic or allergenic reactions; e) no impact on natural defense mechanisms of the body; and f) no impact on the formation of blood platelets, or on the coagulation or denaturalization of plasma proteins.

In other words, the material needs to be compatible from two points of view. The effects of the human body on the implant, as well as the effects of the implant (or substances produced due to corrosion or wear) on the human body must be considered.

The most popular odontological and orthopedic implants are those made of pure titanium or those made with titanium alloys (Ti-6A1-4V) (D. F. Williams, J. Med. Eng. Technol. I (1977) 266–270). Such implants enjoy a high resistance to mechanical stresses together with a resistance to corrosion; this property results from the high affinity of the implants for oxygen, which generates a fine protective oxide coating at ambient temperature. However, this affinity for oxygen makes the cleaning of the implants particularly difficult.

Titanium and titanium alloy implants are bioinert implants. If an interface displacement occurs during the recovery period, the fibrous tissue capsule may be too thick, thus causing a quick loosening of the implant and, finally, causing the implant or the adjacent bone to break (L. L. Hench & J. Wilson, "An Introduction to Bioceramics", ed. By L. L. Hench & J. Wilson, Advance Series in Ceramics-Vol. 1. World Scientific Publishing, Singapore, (1933) 1–24). Furthermore, the metal implants differ significantly, in their mechanical features as well as in their composition, from the osseous tissues where they are to be inserted.

With the purpose of avoiding the disadvantages of metal implants, tests have been conducted on non-metallic materials such as ceramics, polymers, and hybrid materials.

Since the bone mineral phase is made of calcium phosphate, research has been conducted on biocompatible ceramics, and in particular on different types of calcium phosphates (CaP) such as hydroxyapatite, tricalcium phosphate, carbonated hydroxyapatite, apatite, pyrophosphate, and tetracalcium phosphate. The advantage of calcium phosphates is based on their direct coupling to the bone with no fibrous tissue in the interface. This type of material has a high bioactivity (S. Best "Seminar in Bio-Active Materials in Orthopedics" Sep. 27, 1994, Cambridge, UK).

Among these calcium phosphates, the hydroxylapatite (HA), having the formula $Ca_{10}(PO_4)_6(OH)_2$ has generated great interest since for a long time it was believed that it had the same composition as the calcium phosphate of bone. At present it is widely accepted that bone develops a strong coupling with implants made with sintered hydroxylapatite (K. DeGroot, R. Geesink, C.P.A. T. Klein and P. Serekian, Journal of Biomedical Materials Research, Vol. 21, (1987) 1375–1381). Thus, hydroxylapatite has a very high bioactivity.

The main disadvantage in the use of implants made of calcium phosphates is their low resistance to mechanical stresses due to their poor mechanical properties. For this reason the application of calcium phosphate coatings over metal substrates or other materials subject to stress is becoming very common for odontological and orthopedic implants.

The CaP coatings more frequently applied on odontological and orthopedic implants are those made of HA. If the HA coating is pure and thick, i.e., with low porosity, it will not be reabsorbed and the coupling between bone and HA will take place in a 3 to 6 week period. The HA density will depend on the morphology as well as the physical and chemical properties of the HA powder used. The coupling between bone and HA has been proved by tests conducted on animals as well as on humans (R. G. T. Geesink, Ph.D. Thesis, Marquette University, 1974). Furthermore, HA is considered to be an osteoconductive material, meaning that it would force the bone growth in accordance with its own crystal structure.

However, it has been found recently that the CaP composition, forming the bone mineral phase, is not exactly the same as that of HA, for the CaP composition contains carbon in carbonate groups to constitute a carbonated hydroxylapatite (HAC). Also, it has been found that the interface between implants made of different calcium phosphates and the bone is made of the carbonated hydroxylapatite (HAC). The crystal structure of this HAC coincides in practice with that of HA. For this reason, it is thought that this HAC can be a much more bioactive ceramic than HA and possibly, have a higher osteoconductivity. In fact, HAC powders are being produced and sintered for use in implants.

The methods commonly used to produce such coatings are electrophoresis deposition (P. Ducheyne, W. V.

Raemdonck, J. C. Heughebaert & M. Heughebaert, Biomaterials 7 (1986) 97), plasma spraying (S. D. Cook, J. F. Kay, K. A. Thomas, R. C. Anderson, M. C. Reynolds & J. Jarcho, J. Dental Res. 65(1986) 222) and cathodic spraying by radio frequency (E. Ruckenstein, S. Gourisanker & R. E. Baier, J. Colloid and Interface Sci. 63 (1983) 245). The method most commonly used to produce such HA coatings is the plasma spraying method, which creates 50–200 $\mu$m thick coatings with a HA content of 90% in case that the initiation material is 100% HA. The minimum thickness obtained by industrial processes is 50–60 $\mu$m and it is the result of a compromise between minimum thickness and homogeneity, due to the fact that this technique produces very high porosity coatings and, thus, it becomes necessary to deposit successive coatings of approximately 10 $\mu$m in thickness to obtain a uniform granular coating. However, such coatings present the following inconveniences: a) at present it is not possible to get continuous coatings of less than 20 $\mu$m thickness; b) the coatings have a granular morphology, i.e., they have a high porosity; c) due to the coating thickness (50–200 $\mu$m) the adherence to the substrate is very poor; d) as a result of the stresses produced, due to the difference of elongation degree in substrate and coating, frequent cracks appear; and e) some coating areas turn out to be amorphous or microcrystalline (meaning that microcrystals of tricalcium phosphate form) due to high plasma temperatures, thus generating the breakdown and excessive fusion of HA powders. For this reason, such coatings have high absorbance, and it is difficult to control the degree of absorbance.

In practice, and due to flaking problems (which can be caused by low adherence substrate coatings), many surgeons prefer to use, in odontological and orthopedic applications, non-coated implants to avoid the high risk of coating failure.

The laser ablation technique used in the present invention was first used in 1965, only five years after the construction of the first ruby laser. Since then, this technique has been used for the production of coatings with all types of materials (see, for example: D. B. Chrisey & G. K. Hubler ed. "Pulsed laser deposition of thin films", John Wiley and Sons, Inc. New York (1994)). The present invention includes an application of this technique to the field of osteointegrated coatings.

One of the advantages of the present invention is the possibility of applying a gradual composition coating in the Ca—P—H—O—C system, with the option to adapt this coating to the features of the implant or to those of bone in contact with the implant. The coating may have a composition such that the reabsorption rate by the bone is equal to the bone growth rate, thus obtaining an optimum coupling in every moment, and therefore finally providing a perfect osteointegrated implant.

Another advantage of the method of the present invention consists of a substantial improvement in the adherence between the coating and the implant, thus avoiding one of the greatest disadvantages of coatings applied by means of the plasma spraying technique.

Furthermore, the method of the present invention does not negatively impact implant properties since the application temperature is not too high (450° C.) and is relatively low compared to the very high temperatures reached with the plasma used in the plasma spraying technique.

It must also be noted that the coatings applied have a thickness of several microns, thus making it unnecessary to apply any further treatment after deposition (except for sterilization). Therefore, the element treated does not require any further machining, thus reducing the residual stresses that can generate cracks.

The method for improving the osteointegration of osseous fixing implants, which is the object of the present invention, consists of successive treatments to the implant surface.

To better understand the object of the present invention an embodiment of the method for improving the osteointegration of osseous fixing implants is described hereinafter. This method is described in accordance with the enclosed figure where a vacuum chamber is shown to be used for this purpose.

The process is essentially conducted in a vacuum chamber, as shown in the FIGURE. First, the implant, once manufactured, is subjected to cleaning and to passivation treatment. This process can be conducted with acid attack in an ultrasound bath.

Once the cleaning and passivation process is finished, the implant is placed inside a vacuum chamber 1 specifically designed for this process. The basic material used for the coating 4 is placed inside the vacuum chamber 1 and can be rotated during the deposition process by means of a motor 5. The vacuum chamber 1 is connected to the vacuum control system, the controlled flow gas feeding system and the temperature control system, all of which are commonly used in industrial equipment and, therefore, are not shown in the FIGURE. Once this vacuum chamber 1 is closed, a vacuum is applied, typically $10^{-8}$ torr. ($133.3 \times 10^{-6}$Pa) and the implant is moderately heated by means of an appropriate heater 2 inside the vacuum chamber 1. When the required pressure and temperature are reached, the chamber will be filled with an atmosphere in which the deposition process will take place. The atmosphere will depend on the type of material required, and may consist of Ar, $H_2$, $O_2$, $CO_2$, or mixtures thereof. The gases are supplied by means of the gas feeding system 3. Once the required gas composition as well as the required temperature are obtained, the basic material used for the coating 4 is subject to ultraviolet radiation provided by an excimer laser 6. The ultraviolet radiation enters the chamber 1 through a transparent window 8 (which can be made from molten silica). To obtain a high density of ultraviolet radiation energy inside the chamber 1, the laser beam 6 can be focused by means of a lens 7. Due to the laser beam radiation 6, the material used for the coating 4 is ablated and moved towards the implant 9 to create an adhesive coating covering the whole surface of the implant. The gases not used in the process and the residual products are expelled through the gas outlet 10 and conveyed to an adequate gas treatment system (not shown in the FIGURE).

Once the required coating is provided, the implant is conveyed by means of a vacuum handling system (11, 14, and 16) to within a second vacuum chamber 12 where the coated implant is subject to ultraviolet radiation produced by silent discharge excimer lamps 15 with the purpose of sterilizing the implant as well as the container 13. Once the sterilization process is completed, the implant is introduced into the container 13 which is sealed by means of the vacuum handling system 14 and the implant is perfectly vacuum sealed and ready for application.

As an example, the method described can be performed using an excimer laser ($\lambda$=193 nm) operating on 20 Hz pulse mode and with an energy density of 2.5 J/cm$^2$ in a water vapor atmosphere. The total pressure can be 0.45 mbar (45 Pa) and the temperature can be 485° C. The distance coating material-implant can be 0.045 m, and the rotation speed of the coating material can be 1 revolution per minute (rpm). The coating of carbonated calcium phosphate on the pure titanium implant should be deposited at a deposition rate of at least 0.54 A/pulse and it should have an adherence degree to the implant of at least 58 Mpa.

The method described can provide a very tacky $Ca_UP_VH_XO_YC_Z$ film on implants formed with a plurality of materials as, for example, titanium and its alloys, steels, chromium and cobalt alloys, and hybrid materials.

The great flexibility provided by this method allows for the modification of the physical and chemical properties and of the film thickness by merely changing the process parameters. Thus, it will be possible to obtain $Ca_UP_VH_XO_YC_Z$ coatings with different optical, electrical, and mechanical properties, which will be very useful to adapt the coating to specific features of the substrate and to the type of bone that will be in contact with the implant.

This method will allow for an improved osteointegration of the finished implants, with a constant size, so that the parts treated by the method described in the present invention will still meet the allowances previously specified for the implant application.

Once the nature, as well as one embodiment of the present invention have been thoroughly described, it will be possible to introduce changes in the shape, materials, and arrangement of the invention, as long as these changes do not substantially affect the characteristics of the invention as claimed.

What is claimed is:

1. A method for improving the osteointegration of an osseous fixing implant comprising:
    a) cleaning and passivating the implant through acid attack in an ultrasound bath;
    b) introducing the implant and a coating material of $Ca_UP_VH_XO_YC_Z$, where subscripts u, v, x, y, and z are natural numbers including zero with variable stoichiometry, into a first vacuum chamber;
    c) introducing into the first vacuum chamber an atmosphere used in a deposition process, said atmosphere comprising argon, water vapor, oxygen, or mixtures thereof;
    d) irradiating the coating material with ultraviolet photons ($\lambda$=193 nm) provided by an ArF excimer laser by introducing into the first vacuum chamber a laser beam through a window in said first chamber, wherein the window is transparent to said beam resulting in application of the coating material onto the implant surface;
    e) conveying the implant by means of a vacuum control system to a second vacuum chamber which contains a container;
    f) exposing the container and the implant in the second vacuum chamber to ultraviolet radiation to sterilize the container as well as the implant;
    g) introducing the implant into the sterilized container; and
    h) sealing the container with the implant inside to obtain a sterilized vacuum assembly.

2. The method according to claim 1, wherein the first vacuum chamber is provided with a rotating means for holding the implant.

3. The method according to claim 1, wherein an electric field is established between the coating material and the implant.

4. The method according to claim 1, wherein the cleaning and passivating comprise:
    a) cleaning with ketone in an ultrasound bath for 8 minutes;
    b) cleaning with deionized water;
    c) cleaning with $HNO_3$ with a 5% content, in an ultrasound bath for 8 minutes;
    d) cleaning with deionized water; and
    e) cleaning with methanol;
    wherein all of the above processes are conducted at normal pressure and temperature conditions.

5. The method according to claim 1, further comprising subjecting the implant to be coated to ultraviolet radiation during at least one of the time periods before and after introducing an atmosphere, said radiation being produced either by a laser beam, a mercury lamp, a silent discharge excimer lamp, or any other ultraviolet radiation source such that the whole implant surface gets sterilized and chemically activated.

6. The method according to claim 1, wherein two coatings of $Ca_UP_VH_XO_YC_Z$ are applied, and both coatings have different degrees of crystallinity.

7. The method according claim 1, wherein the coating material is deposited with controlled preferential crystallographic orientations.

8. The method according to claim 1, wherein the coating material presents a crystalline or composition degree such that bone growth is stimulated at the same rate that coating reabsorption occurs.

9. The method according to claim 1, wherein the implant to be treated is made of Ti, a Ti alloy, MgO, Si, GaAs, GeSi, SiC, C, a polymer, steel, or a Co—Cr, $Al_2O_3$ alloy.

10. An implant processed by a method according to claim 1.

* * * * *